United States Patent [19]

Horiie et al.

[11] 4,075,253

[45] Feb. 21, 1978

[54] ORGANOLITHIUM POLYMERIZATION INITIATORS AND THEIR PREPARATIONS

[75] Inventors: Shigeki Horiie; Shin-Ichiro Asai; Takashi Torikoshi; Kazuhiro Shirakawa; Minoru Handa, all of Machida, Japan

[73] Assignee: Denki Kagaku Kogyo Kabushiki Kaisha, Tokyo, Japan

[21] Appl. No.: 577,980

[22] Filed: May 15, 1975

[30] Foreign Application Priority Data

May 15, 1974 Japan .................................. 49-54125

[51] Int. Cl.² ................................................ C07F 1/02
[52] U.S. Cl. ............................ 260/665 R; 252/431 L
[58] Field of Search ................. 260/665 R; 252/431 L

[56] References Cited

U.S. PATENT DOCUMENTS

| | | | |
|---|---|---|---|
| 3,091,606 | 5/1963 | Hsieh | 260/94.2 |
| 3,308,170 | 3/1967 | Pritchett et al. | 260/665 R X |
| 3,388,178 | 6/1968 | Kamienski et al. | 260/665 R |
| 3,560,593 | 2/1971 | Hsieh | 260/665 R X |
| 3,663,634 | 5/1972 | Morton | 260/665 R |
| 3,776,964 | 12/1973 | Morrison et al. | 260/665 R |
| 3,848,008 | 11/1974 | Fetters | 260/665 R |

FOREIGN PATENT DOCUMENTS 1,264,741    2/1972    United Kingdom.

*Primary Examiner*—Helen M. S. Sneed
*Attorney, Agent, or Firm*—Sughrue, Rothwell, Mion, Zinn and Macpeak

[57] ABSTRACT

A stable and non-polar solvent soluble alpha-methylstyrene-conjugated diene oligomer dilithium as a polymerization initiator is obtained by preparing a dilithium initiator solution by reacting lithium metal with alpha-methylstyrene in a polar solvent at low temperature, thereafter adding gradually a small amount of a conjugated diene to the dilithium initiator solution to consume completely the alpha-methylstyrene, and then adding additional conjugated diene in a certain amount so as to prepare the stable and non-polar solvent soluble alpha-methylstyrene-conjugated diene oligomer dilithium.

11 Claims, No Drawings

ORGANOLITHIUM POLYMERIZATION INITIATORS AND THEIR PREPARATIONS

BACKGROUND OF THE INVENTION

1. Field of the Invention

This invention relates to novel alpha-methylstyrene-conjugated diene oligomer dilithium as a polymerization initiator. In one aspect, the invention relates to a process for preparing novel alpha-methylstyrene-conjugated diene oligomer dilithium as a polymerization initiator for a living polymerization.

2. Description of the Prior Art

It is well know that organodilithium initiators are used as initiators for the living polymerization, in general, and A. C. S. Polymer Preprints, Vol. 10, No. 2, P 837 (1969) and British Pat. No. 1264741 disclose a preparation of alpha-methylstyrene oligomer dilithium as a polymerization initiator, but the active lithium linking and the terminals of the initiator is very unstable. For example, the initiator loses the greater part of its activity after 24 hours at 25° C. Moreover, the initiator is not soluble in a non-polar solvent, and unreacted alpha-methylstyrene monomer remains in the initiator. Consequently, the initiator is not suitable for a living polymerization as a polymerization initiator. Further, U.S. Pat. No. 3,091,606 discloses a process for solubilizing a polymerization initiator by the addition of dienes. However, in a process where a diene is added all at once, it is impossible to obtain a stable active terminal lithium because gellation occurrs.

SUMMARY OF THE INVENTION

It is an object of this invention to provide a non-polar solvent soluble alpha-methylstyrene-conjugated diene oligomer dilithium as a polymerization initiator for a living polymerization.

Another object of the invention is to provide alpha-methylstyrene-conjugated diene oligomer dilithium in which the active lithium is stable.

A further object of the invention is to provide an improved process for preparing a polymerization initiator for a living polymerization.

A still further object of the invention is to provide alpha-methylstyrene-conjugated diene oligomer dilithium having a block structure comprising tetramer units in the central portion of the polymeric chain.

These and other objects and advantages of the invention will become apparent to those skilled in the art upon consideration of the accompanying disclosure.

This invention in one embodiment provides a process which comprises preparing a dilithium initiator solution by reacting lithium metal with alpha-methylstyrene in a solvent at a temperature of about −20° to +30° C wherein about 0.25 to 2.0 gram atoms of lithium metal per mole of the alpha-methylstyrene are used, thereafter adding gradually a small amount of a conjugated diene to the dilithium initiator solution so as to consume completely the unreacted alpha-methylstyrene and simultaneously obtain an alpha-methylstyrene-conjugated diene oligomer dilithium, and then adding at least two additional moles of the conjugated diene to the alpha-methylstyrene-conjugated diene oligomer dilithium in order to prepare a non-polar solvent soluble and stable alpha-methylstyrene-conjugated diene oligomer dilithium.

This invention in another embodiment provides a stable and non-polar solvent soluble alpha-methylstyrene conjugated diene oligomer dilithium represented by the general formula $$Li - C - B - A - B - C - Li$$

wherein A represents a central homopolymer block of alpha-methyl-styrene, B represents a random copolymer block of alpha-methylstyrene and a conjugated diene and C represents a homopolymer block of the conjugated diene, with an active lithium on the terminals of the homopolymer block of the conjugated diene.

DETAILED DESCRIPTION OF THE INVENTION

In greater detail, in the process according to the invention the dilithium initiator solution is prepared first by reacting lithium metal with alpha-methylstyrene in a polar solvent at a temperature of about −20° to +30° C. In this case, alpha-methylstyrene oligomer dilithium and unreacted alpha-methylstyrene monomer co-exist in the solution since a reaction equilibrium is established between the oligomer and monomer. Then, conjugated diene is added to the dilithium initiator solution in order to complete the reaction of the unreacted alpha-methylstyrene monomer, and then conjugated diene is further added to the dilithium initiator solution so as to prepare the non-polar solvent soluble and stable alpha-methylstyrene-conjugated diene oligomer dilithium as the polymerization initiator for the living polymerization.

The process of the invention can be carried out at a temperature within the range of about −20° to +30° C. However, it is preferred to carry out the process at a temperature in the range of −5° to +10° C. At a temperature higher than about +30° C, the active lithium linking the terminals of the alpha-methylstyrene-conjugated diene oligomer dilithium is easily deactivated and at a temperature less than about −20° C, the consumption of lithium metal is reduced, and the oligomer becomes a high polymer.

The amount of lithium metal in the reaction of the alphamethylstyrene and lithium metal is in the range of about 0.25 to 2.0 gram atoms, preferably 0.4 to 0.7 gram atom, per mole of the alpha-methylstyrene. If an amount of less than about 0.25 gram atom is used, the alpha-methylstyrene oligomer dilithium obtained becomes a gel-like polymer so that the solubility of of the oligomer in a solvent decreases and while if more than about 2.0 gram atoms is used the consumption of lithium metal is less than 20 mole %.

The lithium employed for preparing the initiator can be used in any form, such as a wire, chunks, shot, powder or dispersion.

The alpha-methylstyrene employed in the reaction of lithium metal should be added at a rate of addition ranging from about 0.06 mole to 2.0 moles, preferably about 0.25 mole to 0.65 mole, per gram atom of lithium metal per hour.

That is, when the alpha-methylstyrene is added all at once a gelation of the reaction solution obtained takes place immediately.

If an amount less than about 0.06 mole per gram atom per hour is added, the active lithium is deactivated and if an amount more than 2.0 moles per gram atom per hour is added the consumption of lithium metal is reduced and the oligomer becomes gel like.

The conjugated diene should be added to consume completely the unreacted alpha-methylstyrene monomer. If the unreacted alpha-methylstyrene monomer is not consumed, the unreacted alpha-methylstyrene monomer remains in the finally synthesized alpha-methylstyrene-conjugated diene oligomer dilithium as the polymerization initiator for the living polymerization so that the polymerization initiator becomes unstable and inactive because the terminals of the copolymerized conjugated diene are replaced by unreacted alpha-methylstyrene. At least about 0.2 mole, preferably 0.2 moles to 1.0 mole, of the conjugated diene, per mole of alpha-methylstyrene oligomer dilithium is added gradually over a period of more than one hour at a temperature of about − 20° to + 30° C. When the amount of the conjugated diene is less than about 0.2 mole, unreacted alpha-methylstyrene monomer remains. Further, additional conjugated diene is added at a temperature of about − 20° to + 30+ C to the alpha-methylstyrene-conjugated diene oligomer dilithium which is obtained after the copolymerization of alpha-methylstyrene and conjugated diene in order to prepare a stable and non-polar solvent soluble alpha-methylstyrene-conjugated diene oligomer dilithium. The amount of the conjugated diene to be additionally added is in the range of about 2 moles to 20 moles per mole of the alpha-methylstyrene-conjugated diene oligomer dilithium. When the amount of the conjugated diene is less than about 2 moles, the remaining chain terminals of unreacted alpha-methylstryene become easily unstable and it is difficult to dissolve the product in a non-polar solvent.

The solvents to be employed according to the invention include polar solvents and non-polar solvents. Examples of polar solvents which can be advantageously employed are dimethyl ether, diethyl ether, ethyl methyl ether, ethyl propyl ether, di-n-propyl ether, di-n-octyl-ether, dioxane, 1,2-dimethoxyethane, diphenyl ether, tetrahydrofuran, dimethylethylamine, tri-n-propylamine, tri-n-butylamine, trimethylamine, triethylamine, and the like. Non-polar solvents which can be employed are isobutane, n-pentane, isooctane, n-dodecane, cyclohexane, methyl-cyclohexane, ethylcyclohexane, dimethylcyclopentane, benzene, toluene, xylene, ethyl benzene, and the like. It is to be understood also that mixtures of these solvents can also be employed in the practice of the present invention.

Examples of conjugated dienes which can be used in preparing alpha-methylstyrene-conjugated diene oligomer dilithium are 1,3-butadiene, isoprene, 2,3-dimethyl-1,3-butadiene, piperylene, 2-methyl-3-ethyl-1,3-butadiene, 3-methyl-1,3-pentadiene, 2-methyl-3-ethyl-1,3-pentadiene, 3-methyl-1,3-pentadiene, 1,3-hexadiene, 2-methyl-1,3-hexadiene, 1,3-heptadiene, 3-methyl-1,3-heptadiene, 1,3-octadiene, 3-butyl-1,3-octadiene, 3,4-dimethyl-1,3-hexadiene, 3-n-propyl-1,3-pentadiene, 4,5-diethyl-1,3-octadiene, phenyl-1,3-butadiene, 2,3-diethyl-1,3-butadiene, 2,3-di-n-propyl-1,3-butadiene, 2-methyl-3-isopropyl-1,3-butadiene, and the like.

The alpha-methylstyrene-conjugated diene oligomer dilithium obtained by removing the polar solvents or non-polar solvents from the alpha-methylstyrene-conjugated diene oligomer dilithium solution obtained by distillation under reduced pressure is soluble in a non-polar solvent and can beused as the polymerization initiator for the living polymerization.

The alpha-methylstyrene-conjugated diene oligomer dilithium prepared by the process according to the invention is composed of three different block structures represented by the general formula

where A represents a central homopolymer block of alpha-methylstyrene, B represents a random copolymer block of alpha-methylstyrene and a conjugated diene and C represents a homopolymer block of the conjugated diene, with an active lithium on the terminals of the homopolymer block of the conjugated diene.

The homopolymer block of alpha-methylstyrene is composed essentially of a tetramer and that of the conjugated diene is composed of a polymer which ranges from a monomer to a decamer.

A more comprehensive understanding of the invention can be obtained by referring to the following illustrative examples which are not intended, however, to be construed as limiting the invention. Unless otherwise indicated herein, all parts, percents, ratios and the like are by weight.

EXAMPLE I

The formulation employed was as follows:

| | |
|---|---|
| Lithium Dispersion | 7 g |
| Alpha-methylstyrene | 236 g |
| Butadiene (initially added) | 20 g |
| Butadiene (subsequently added) | 135 g |
| Tetrahydrofuran (THF) as a solvent | 500 ml |

The 7 g of lithium dispersion was added to the 500 ml of tetrahydrofuran under an atmosphere of purified high purity $N_2$. The 236 g of alpha-methylstyrene was added slowly over a period of 4 hours at 0° C. As soon as the alpha-methylstyrene had been added, a light red color formed. The obtained dilithium alpha-methylstyrene oligomer initiator solution remained in a liquid state.

The concentration of the active lithium in the initiator solution which were measured by the Gillman double titration method (J. Am. Chem. Soc., 66, 1515 (1944) were 0.93 mole/1 and the consumption of lithium metal was 71 mole %. The amount of unreacted alpha-methylstyrene was 12 wt%.

The initiator solution was treated with methanol and the molecular weight distribution of the reaction products obtained was measured using gel permeation chromatography (G.P.C.). As a result, the reaction products were alpha-methylstyrene oligomer dilithium having a very simple molecular weight distribution which was composed of tetramers and a few pentamers.

After 20 g of butadiene were gradually added over a period of 1.5 hours at 0° C to the initiator solution, as a result of analyzing the reaction solution obtained using the chromatography no alpha-methylstyrene monomer was found to be present in the reaction solution.

Then the additional 135 g of butadiene was added over a period of 2 hours at 0° C to the reaction solution. As a result of analyzing the reaction solution obtained using ultraviolet spectral analysis the end peaks of alpha-methylstyrene-lithium metal at 340 m$\mu$ disappeared, and new end peaks of butadiene-lithium metal appeared at 288 m$\mu$. By distillation under reduced pressure tetrahydrofuran was removed from the reaction solution, and 500 ml of benzene were added when the temperature reached 50° C and then the alpha-methylstyrene-butadiene oligomer dilithium obtained was dissolved in benzene over a period of 3 hours under atmospheric pressure at 50° C and a uniform polymerization initiator was obtained.

The concentration of the active lithium in the initiator solution was 0.72 mole/l and the tetrahydrofuran remaining was 1.2 wt%. The stability of the initiator solution was measured at 25° C with the concentration of the active lithium as a parameter.

The results obtained are shown in Table I.

The measurement was carried out by measuring the change of the concentrations of the active lithium at various time intervals and changes in the concentrations were measured up to 24 hours.

Table I

| | (at 25° C) Time (hours) | | | |
| --- | --- | --- | --- | --- |
| | 0 | 6 | 14 | 24 |
| Active Lithium Concentration (mole/l) | 0.72 | 0.72 | 0.72 | 0.72 |

EXAMPLE II

The formulation employed was as follows:

| | |
| --- | --- |
| Lithium Dispersion | 7 g |
| Alpha-methylstyrene | 236 g |
| Isoprene (initially added) | 40 g |
| Isoprene (subsequently added) | 250 g |
| Triethylamine as a solvent | 500 ml |

The reaction procedure was the same as that in Example 1. The concentration of active lithium in the alpha-methylstyrene oligomer dilithium obtained was 0.86 mole/l and the consumption of lithium metal was 66 mole %.

The unreacted alpha-methylstyrene monomer was 15 wt %. The alpha-methylstyrene oligomer dilithium had a very narrow molecular weight distribution which was composed of tetramers and a few pentamers.

After the 40g of isoprene was gradually added over a period of 1.5 hours at 0° C to the initiator solution, no alpha-methylstyrene monomer was found to be present in the reaction solution.

Then the additional 250 g of isoprene was added over a period of 2 hours at 0° C to the reaction solution and the end peaks of alpha-methylstyrene indicated by ultraviolet spectral analysis disappeared.

By distillation under reduced pressure triethylamine was removed from the reaction solution and 500 ml of cyclohexane was added and then the alpha-methylstyrene-isoprene oligomer dilithium obtained was dissolved in cyclohexane over a period of 3 hours at atmospheric pressure at 50° C and a uniform polymerization initiator solution was obtained.

The concentrations of the active lithium in the solution were 0.59 mole/l and the triethylamine remaining was 1.5 wt %.

The changes in the lithium concentration were measured up to 24 hours. The results obtained are shown in Table II.

Table II

| | (at 25° C) Time (hours) | | | |
| --- | --- | --- | --- | --- |
| | 0 | 6 | 14 | 24 |
| Active Lithium Concentration (mole/l) | 0.59 | 0.59 | 0.59 | 0.59 |

EXAMPLE III

The formulation employed was as follows:

| | |
| --- | --- |
| Lithium | 7 g |
| Alpha-methylstyrene | 236 g |
| Butadiene (initially added) | 15 g |
| Butadiene (subsequently added) | 140 g |
| THF as a solvent | 150 ml |
| Benzene as a solvent | 350 ml |

The reaction procedure was the same as that in Example I. The concentrations of active lithium in the alpha-methylstyrene oligomer dilithium obtained were 0.90 mole/l and the consumption of lithium metal was 64 mole %.

The unreacted alpha-methylstyrene monomer was 10 wt %.

The alpha-methylstyrene oligomer dilithium had a very narrow molecular weight distribution which was composed of tetramers and a few pentamers.

After the 15 g of butadiene was gradually added over a period of 1.5 hours at 0° C to the initiator solution, alpha-methylstyrene monomer was found to be completely consumed in the reaction solution.

The additional 140 g of butadiene was added over a period of 2 hours at 0° C to the reaction solution and the end peaks of alpha-methylstyrene indicated by ultraviolet spectral analysis disappeared.

By distillation under reduced pressure, the tetrahydrofuran and benzene were removed from the reaction solution and 500 ml of benzene were added and then a uniform polymerization initiator solution was obtained. The concentration of the active lithium is the solution was 0.70 mole/l and the tetrahydrofuran remaining was 1.0 wt %.

The changes of the active lithium concentration were observed up to 24 hours. The results obtained are shown in Table III.

Table III

| | (at 25° C) Time (hours) | | | |
| --- | --- | --- | --- | --- |
| | 0 | 6 | 14 | 24 |
| Active Lithium Concentration (mole/l) | 0.70 | 0.70 | 0.70 | 0.70 |

Comparative Example I

The formulation used was as follows:

| | |
| --- | --- |
| Lithium Dispersion | 7 g |
| Alpha-methylstyrene | 236 g |
| Butadiene (initially added) | 20 g |
| Butadiene (subsequently added) | 40 g |
| THF as a solvent | 500 ml |

The 7 g of the lithium dispersion was added to 500 ml of tetrahydrofuran under an atmosphere of purified high purity $N_2$. The 236 g of alpha-methylstyrene was added slowly over a period of 4 hours at 0° C. The concentration of active lithium in the alpha-methylstyrene oligomer dilithium obtained was 0.93 mole/l and the consumption of lithium metal was 71 mole %. The unreacted alpha-methylstyrene was 12 wt %. The molecular weight distribution of the reaction product was a very narrow, and the product was found to be composed of tetramers and a few pentamers.

After the 20 g butadiene was gradually added over a period of 1.5 hours at 0° C to the initiator solution, as a result of gas chromatographic analysis no alpha-methylstyrene monomer was found to be present in the reaction solution.

Then the additional 40 g of butadiene was added over a period of 0.5 hour at 0° C to the reaction solution.

As a result of analyzing the reaction solution obtained with ultra-violet spectral analysis the end peaks of alpha-methylstyrene lithium metal at 340 m$\mu$ were decreased up to 35%.

By distillation under reduced pressure tetrahydrofuran was removed from the reaction solution and 500 ml of benzene were added and then a polymerization initiator solution was obtained.

Then concentration of the active lithium in the solution was 0.65 mole/l and tetrahydrofuran remaining was 1.7 wt %.

The change of the active lithium concentration was evaluated up to 24 hours. The results obtained are shown in Table IV.

Table IV

|  | (at 25° C) Time (hours) | | | |
| --- | --- | --- | --- | --- |
|  | 0 | 6 | 14 | 24 |
| Active Lithium Concentration (mole/l) | 0.65 | 0.50 | 0.43 | 0.40 |

Comparative Example II

The formulation employed was as follows:

| Lithium Dispersion | 7 g |
| --- | --- |
| Alpha-methylstyrene | 236 g |
| Butadiene (initially added) | None |
| Butadiene (subsequently added) | 135 g |
| THF as a solvent | 500 ml |

The 7 g of the lithium dispersion was added to 500 ml of tetrahydrofuran under an atmosphere of purified high purity $N_2$. The 236 g of alpha-methylstyrene was added slowly over a period of 4 hours at 0° C. The concentration of active lithium in the alpha-methylstyrene oligomer dilithium obtained was 0.93 mole/l and the consumption of lithium metal was 71 mole %.

The unreacted alpha-methylstyrene was 12 wt %.

Then the 135 g of butadiene was added over a period of 0.5 hour at 0° C to the reaction solution.

As a result of gas chromatographic analysis, the amount of alpha-methylstyrene monomer present was found to be 8 wt % and using ultra-violet spectral analysis the end peaks of alpha-methylstyrene-lithium at 340 m$\mu$ were found to be decreased to 6%.

Tetrahydrofuran was removed from the reaction solution by distillation under reduced pressure and 500 ml of benzene was added and then a polymerization initiator solution was obtained.

The concentration of the active lithium in the solution was 0.61 mole/l and tetrahydrofuran remaining and alpha-methylstyrene monomer were 2.3 wt and 6 wt %, respectively.

The change in the active lithium concentration was measured up to 24 hours. The results obtained are shown in Table V.

Table V

|  | (at 25° C) Time (hours) | | | |
| --- | --- | --- | --- | --- |
|  | 0 | 6 | 14 | 24 |
| Active Lithium Concentration (mole/l) | 0.61 | 0.53 | 0.46 | 0.31 |

Comparative Example III

The formulation employed was as follows:

| Lithium Dispersion | 7 g |
| --- | --- |
| Alpha-methylstyrene | 236 g |
| Butadiene (initially added) | None |
| Butadiene (subsequently added) | None |
| THF as a solvent | 500 ml |

The 7 g of the lithium dispersion was added to 500 ml of tetrahydrofuran under an atmosphere of purified high purity $N_2$. 236 g of alpha-methylstyrene was added slowly over a period of 4 hours at 0° C. The concentration of the active lithium in the alpha-methylstyrene oligomer dilithium obtained was 0.93 mole/l and the consumption of lithium metal was 71 mole %.

The unreacted alpha-methylstyrene was 12 wt %.

Tetrahydrofuran was removed by distillation under reduced pressure from the reaction solution and 500 ml of benzene were added. This alpha-methylstyrene oligomer dilithium was not soluble in benzene, and the oligomer became a slurry. The concentration of the active lithium in the solution was 0.68 mole/l and tetrahydrofuran remaining was 2.5 wt %. The change of the active lithium concentration was measured up to 24 hours. The results obtained are shown in Table VI.

Table VI

|  | (at 25° C) Time (hours) | | | |
| --- | --- | --- | --- | --- |
|  | 0 | 6 | 14 | 24 |
| Active Lithium Concentration (mole/l) | 0.68 | 0.51 | 0.39 | 0.21 |

Comparative Example IV

The formulation employed was as follows:

| Lithium Dispersion | 7 g |
| --- | --- |
| Alpha-methylstyrene | 236 g |
| Butadiene (initially added) | None |
| Butadiene (subsequently added) | None |
| THF as a solvent | 160 ml |
| Benzene as a solvent | 280 ml |

The 7 g of lithium dispersion was added to the mixture of 160 ml of THF and 280 ml of benzene under an atmosphere of purified high purity $N_2$. The 236 g of alpha-methylstyrene were added all at once at 0° C. The temperature of the reaction solution obtained increased to 70° C and a gelatin took place immediately. The concentration of the active lithium in the solution was 0.06 mole/l and the consumption of lithium metal was 4 mole %.

As a result of analyzing the reaction solution obtained using G.P.C, the molecular weight distribution of the reaction product was found to be larger than hexamers.

EXAMPLE IV

A styrene-butadiene block copolymer was prepared by using the initiator obtained in Examples I, II and III and Comparative Examples I and II, respectively. The formulation employed as follows.

| | |
|---|---|
| Styrene | 240 g |
| Butadiene | 60 g |
| Benzene | 1500 g |
| Initiator (used 24 hours after preparation) | 6 millimole |

Under an inert gas atmosphere, the initiator (6 millimole), was charged into a 3l-autoclave equipped with a stirrer at a temperature of 50° C and mixed with 1500 g of the pre-charged benzene, 240 g of styrene and the 40 g of butadiene. Polymerization was carried out for 2 hours and then the polymer was separated with methanol and was dried under reduced pressure. The properties of the block copolymers obtained are shown in Table VII.

Table VII

| Initiator | Tensile Strength (kg/cm$^2$) [JISK-6871] | Elongation (%) [JISK-0871] | Impact Strength (kg.cm/cm$^2$) [DIN53453] | Rock well Hardness (R-scale) (g) [ASTM-D-785] | Styrene[1] Block Ratio (%) | Butadiene[2] (micro-structure) | | | Glass Transition Temperature of Rubber Phase[3] (° C) |
|---|---|---|---|---|---|---|---|---|---|
| | | | | | | cis-1,4 (%) | trans-1,4 (%) | 1,2-vinyl (%) | |
| Example | | | | | | | | | |
| I | 270 | 100 | 110 | 90 | 72 | 35 | 47 | 18 | −12 |
| II | 266 | 110 | 100 | 85 | 68 | 31 | 50 | 19 | −10 |
| III | 281 | 96 | 105 | 92 | 75 | 37 | 47 | 16 | −13 |
| Comparative Example | | | | | | | | | |
| I | 145 | 62 | 46 | 81 | 70 | 32 | 49 | 19 | −10 |
| II | 125 | 75 | 30 | 75 | 62 | 30 | 46 | 24 | − 5 |
| III | 116 | 25 | 10 | 73 | 62 | — | 46 | 25 | − 3 |

EXAMPLE V

The procedure used was the same as that of Example IV.
The formulation used was as follows:

| | |
|---|---|
| Styrene | 80 g |
| Butadiene | 120 g |
| Benzene | 1500 g |
| Initiator (used 24 hours after preparation) | 4 mmole |

The properties of the block copolymers obtained are shown in Table VIII.

Table VIII

| Initiator | Tensile Strength (kg/cm$^2$) [JISK-6301] | Elongation (%) [JISK-6301] | Butadiene (micro-structure) | | | Permanent Set (%) [JISK-6301] |
|---|---|---|---|---|---|---|
| | | | cis-1,4 (%) | trans-1,4 (%) | 1,2-vinyl (%) | |
| Example | | | | | | |
| I | 220 | 860 | — | 46 | 17 | 20 |
| II | 215 | 890 | 33 | 50 | 17 | 21 |
| III | 224 | 850 | 37 | 48 | 15 | 19 |
| Comparative Example | | | | | | |
| I | 80 | 1200 | 28 | 46 | 26 | 32 |
| II | 56 | 1280 | 31 | 46 | 23 | 38 |
| III | 35 | 1400 | 27 | 50 | 23 | 40 |

While the invention has been described in detail and with reference to specific embodiments thereof, it will be apparent to one skilled in the art that various changes and modifications can be made therein without departing from the spirit and scope thereof.

What is claimed is:

1. A process for preparing a polymerization initiator which comprises preparing a dilithium initiator solution by reacting lithium metal with alpha-methylstyrene in a polar solvent at a temperature of about −20° C to +30° C in a ratio of about 0.25 to 2.0 gram atoms of lithium metal per mole of said alpha-methylstyrene wherein the rate of addition of the alpha-methylstyrene ranges from about 0.06 mole to 2.0 moles per gram atom of lithium metal per hour, thereafter adding gradually at least 0.2 mole of a conjugated diene over a period more than about one hour at a temperature of about −20° C to +30° C to said dilithium initiator solution so as to consume completely any unreacted alpha-methylstyrene monomer and simultaneously obtain alpha-methylstyrene-conjugated diene oligomer dilithium, and then additionally adding at least two moles of said conjugated diene at a temperature of about −20° C to +30° C to said alpha-methylstyrene-conjugated diene oligomer dilithium so as to prepare a stable and non-polar solvent soluble alpha-methylstyrene-conjugated diene oligomer dilithium.

2. The process of claim 1, wherein said lithium metal is employed in an amount of 0.4 to 0.7 gram atom per mole of said alpha-methylstyrene.

3. The process of claim 1, wherein said conjugated diene for the completion of the reaction of unreacted alpha-methylstyrene monomer is employed in an amount of 0.2 mole to 1.0 mole per mole of alpha-methylstyrene oligomer dilithium.

4. The process of claim 1, wherein the amount of said conjugated diene added for the preparation of a stable and non-polar solvent soluble alpha-methylstyrene-conjugated diene oligomer dilithium ranges from about 2 moles to 20 moles per mole of said alpha-methylstyrene conjugated diene dilithium oligomer.

5. The process of claim 1, wherein said temperature ranges from −5° C to +10° C.

6. The process of claim 1, wherein the rate of addition of the alpha-methylstyrene ranges from about 0.25 mole to 0.65 mole per gram atom of lithium metal per hour.

7. A stable and non-polar solvent soluble alpha-methylstyrene conjugated diene oligomer dilithium represented by the following general formula:

where A represents a central homopolymer block of alpha-methylstyrene which is substantially a tetramer, B represents a random copolymer block of alpha-methylstyrene and a conjugated diene and C represents a conjugated diene which ranges from a monomer to a decamer, with an active lithium on the terminals of the conjugated diene.

8. The process of claim 1, wherein said conjugated diene is selected from the group consisting of 1,3-butadiene, isoprene, 2,3-dimethyl-1,3-butadiene, piperylene, 2-methyl-3-ethyl-1,3-butadiene, 3-methyl-1,3-pentadiene, 2-methyl-3-ethyl-1,3-pentadiene, 3-methyl-1,3-pentadiene, 1,3-hexadiene, 2-methyl-1,3-hexadiene, 1,3-heptadiene, 3-methyl-1,3-heptadiene, 1,3-octadiene, 3-butyl-1,3-octadiene, 3,4-dimethyl-1,3-hexadiene, 3n-propyl-1,3-pentadiene, 4,5-diethyl-1,3-octadiene, phenyl-1,3-butadiene, 2,3-diethyl-1,3-butadiene, 2,3-di-n-propyl-1,3-butadiene and 2-methyl-3-isopropyl-1,3-butadiene.

9. The stable and non-polar solvent soluble alpha-methylstyrene conjugated diene oligomer dilithium of claim 7, wherein said conjugated diene is selected from the group consisting of 1,3-butadiene, isoprene, 2,3-dimethyl-1,3-butadiene, piperylene, 2-methyl-3-ethyl-1,3-butadiene, 3-methyl-1,3-pentadiene, 2-methyl-3-ethyl-1,3-pentadiene, 3-methyl-1,3-pentadiene, 1,3-hexadiene, 2-methyl-1,3-hexadiene, 1,3-heptadiene, 3-methyl-1,3-heptadiene, 1,3-octadiene, 3-butyl-1,3-octadiene, 3,4-dimethyl-1,3-hexadiene, 3-n-propyl-1,3-pentadiene, 4,5-diethyl-1,3-octadiene, phenyl-1,3-butadiene, 2,3-diethyl-1,3-butadiene, 2,3-di-n-propyl-1,3-butadiene and 2-methyl-3-isopropyl-1,3-butadiene.

10. The process of claim 1, wherein said conjugated diene is butadiene or isoprene.

11. The stable and non-polar solvent soluble alpha-methylstyrene conjugated diene oligomer dilithium of claim 7, wherein said conjugated diene is butadiene or isoprene.

* * * * *

UNITED STATES PATENT OFFICE
CERTIFICATE OF CORRECTION

Patent No. 4,075,253　　　　Dated February 21, 1978

Inventor(s) SHIGEKI HORIIE ET AL

It is certified that error appears in the above-identified patent and that said Letters Patent are hereby corrected as shown below:

Columns 9 and 10, after Table VII insert

--(1) Styrene block ratio (%) = $\dfrac{\text{Quantity of block styrene}}{\text{Total quantity of styrene}} \times 100$ (The block ratio of the styrene portion in the block copolymer was measured by NMR analysis.)

(2) The micro-structure of butadiene was measured using an IR method.

UNITED STATES PATENT OFFICE
CERTIFICATE OF CORRECTION

Patent No. 4,075,253     Dated February 21, 1978

Inventor(s) SHIGEKI HORIIE ET AL

It is certified that error appears in the above-identified patent and that said Letters Patent are hereby corrected as shown below:

(3) ASTM-D-2236-69.--

Signed and Sealed this

Twenty-sixth Day of September 1978

[SEAL]

Attest:

RUTH C. MASON
Attesting Officer

DONALD W. BANNER
Commissioner of Patents and Trademarks